(12) United States Patent
Strober et al.

(10) Patent No.: US 9,504,717 B2
(45) Date of Patent: Nov. 29, 2016

(54) COMBINED ORGAN AND HEMATOPOIETIC CELLS FOR TRANSPLANTATION TOLERANCE OF HLA MISMATCHED GRAFTS

(71) Applicant: The Board of Trustees of the Leland Stanford Junior University, Palo Alto, CA (US)

(72) Inventors: Samuel Strober, Stanford, CA (US); Robert Lowsky, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 133 days.

(21) Appl. No.: 14/175,832

(22) Filed: Feb. 7, 2014

(65) Prior Publication Data
US 2014/0243577 A1    Aug. 28, 2014

Related U.S. Application Data

(60) Provisional application No. 61/769,596, filed on Feb. 26, 2013.

(51) Int. Cl.
| | |
|---|---|
| *A61K 35/28* | (2015.01) |
| *A61K 35/26* | (2015.01) |
| *A61K 35/22* | (2015.01) |
| *A61K 35/14* | (2015.01) |
| *A61K 38/19* | (2006.01) |
| *A61K 41/00* | (2006.01) |
| *A61K 45/06* | (2006.01) |
| *A61K 35/12* | (2015.01) |

(52) U.S. Cl.
CPC ............. *A61K 35/28* (2013.01); *A61K 35/14* (2013.01); *A61K 35/22* (2013.01); *A61K 38/193* (2013.01); *A61K 41/00* (2013.01); *A61K 45/06* (2013.01); *A61K 2035/124* (2013.01)

(58) Field of Classification Search
None
See application file for complete search history.

(56) References Cited

U.S. PATENT DOCUMENTS

| | | | |
|---|---|---|---|
| 8,916,147 B2 * | 12/2014 | Reisner ............... | A61K 35/26 424/93.71 |
| 2011/0110909 A1 | 5/2011 | Ildstad et al. | |
| 2012/0177621 A1 | 7/2012 | Strober et al. | |
| 2012/0329668 A1 * | 12/2012 | Sarwal ............... | C12Q 1/6883 506/9 |

FOREIGN PATENT DOCUMENTS

| | | |
|---|---|---|
| WO | 03/012060 A2 | 2/2003 |
| WO | 2011/068829 A1 | 6/2011 |
| WO | WO 02040640 * | 11/2011 |

OTHER PUBLICATIONS

Millan et al Transplantation, 2002, v.73, pp. 1386-1391.*
Arbab et al. "Efficient magnetic cell labeling with protamine sulfate complexed to ferumoxides for cellular MRI" Blood. Aug. 15, 2004;104(4):1-22.
Perez-Pujol, "Proteomic analysis of gray platelet syndrome by iTRAQ Labelling and mass spetroscopy: a potential new diagnostic strategy for platelet disorders" Blood (ASH Annual Meeting Abstracts) (2005) 106: Abstract 2161.
June et al. "Adoptive T cell therapy for cancer in clinic" J Clin Invest. Jun. 2007;117(6):1466-76.
Leventhal et al. "Chimerism and tolerance without GVHD or engraftment syndrome in HLA-mismatched combined kidney and hematopoietic stem cell transplantation" Sci Transl Med. (Mar. 7, 2012) ;4(124): 1-22.
Scandling et al. "Tolerance and withdrawal of immunosuppressive drugs in patients given kidney and hematopoietic cell transplants" Am J Transplant. (May 2012) ;12(5):1133-45.
Strober et al. "Translational studies in hematopoietic cell transplantation: treatment of hematologic malignancies as a stepping stone to tolerance induction", Semin Immunol. (Aug. 2011) ;23(4):273-81.
Szabolcs et al. "Tolerance after solid organ and hematopoietic cell transplantation", Biol Blood Marrow Transplant. (Jan. 2012) ;18(1 Suppl):S193-200.
Millan et al., "Mixed chimerism and immunosuppressive drug withdrawal after HLA-mismatched kidney and hematopoietic progenitor transplantation", Transplantation, May 2002, pp. 1386-1391, vol. 73, Lippincott Williams & Wilkins, Philadelphia, PA.
Kohrt et al., "TLI and ATG 1-15 Conditioning with Low Risk of Graft-Versus-Host Disease Retains Antitumor Reactions after Allogeneic Hematopoietic Cell Transplantation from Related and Unrelated Donors", Blood, Jul. 30, 2009, pp. 1099-1109, vol. 114, No. 5, The American Society of Hematology, Washington, DC.
Arbab et al., "Efficient magnetic cell labeling with protamine sulfate complexed to ferumoxides for cellular MRI", Blood, Aug. 15, 2004, pp. 1217-1223, vol. 104, No. 4, American Society of Hematology, Washington, DC.
Levanthal et al., "Chimerism and tolerance without GVHD or engraftment syndrome in HLA-mismatched combined kidney and hematopoietic stem cell transplantation", Science Translational Medicine, Mar. 7, 2012, pp. 1-22, vol. 4, No. 124, AAAS, Washington, D.C.
Scandaling et al., "Tolerance and withdrawal of immunosuppressive drugs in patients given kidney and hematopoietic cell transplants", Am J Transplant, May 2012, pp. 1133-1145, vol. 12, No. 5, Wiley, Hoboken, NJ.

(Continued)

*Primary Examiner* — Michail Belyavskyi
(74) *Attorney, Agent, or Firm* — Pamela J. Sherwood; Bozicevic, Field & Francis LLP

(57) ABSTRACT

Methods and compositions are provided for combined transplantation of a solid organ and hematopoietic cells to an HLA mismatched recipient, where tolerance to the graft is established through development of a persistent mixed chimerism. An individual with persistent mixed chimerism, usually for a period of at least six months, is able to withdraw from the use of immunosuppressive drugs after a period of time sufficient to establish tolerance.

12 Claims, 3 Drawing Sheets

(56) References Cited

OTHER PUBLICATIONS

Leventhal et al. "Tolerance Induction in HLA Disparate Living Donor Kidney Transplantation by Donor Stem Cell Infusion: durable chimerism predicts outcome" Transplantation, Jan. 15, 2013 pp. 169-176, 95(1), Lippincott Williams & Wilkins, Philadelphia, PA.

Kawai et al. "HLA-mismatched Renal Transplantation without Maintenance Immunosuppression" The New England Journal of Medicine, Jan. 24, 2008, pp. 353-361, 358(4), Massachusetts Medical Society, Waltham, MA.

Scandling et al., "Chimerism, Graft Survival, and Withdrawal of Immunosuppressive Drugs in HLA Matched and Mismatched Patients After Living Donor Kidney and Hematopoietic Cell Transplantation", American Journal of Transplantation, 2015, pp. 695-704,15, Wiley Periodicals Inc., Hoboken, NJ.

* cited by examiner

Protocol 3: Haplo matched Patient Characteristics, Conditioning, and Donor Cell Composition

| Patients* | Age/Gender | ESRD Cause | Total Dose TLI (cGy) | CD34+ Cell Dose (x10⁶/kg) | CD3+ Cell Dose (x10⁶/kg) | Serum creatinine at last observation (mg/dL) | Duration of chimerism |
|---|---|---|---|---|---|---|---|
| 1 (28 mo) | 47/M | IgA | 1200 | 11.8 | 5 | 1.7 | 1 mo |
| 2 (10 mo) | 24/F | SLE | 1200 | 14.5 | 10 | 0.9 | 10 mo |
| 3 (8 mo) | 35/F | Unknown | 1200 | 21.9 | 10 | 1.0 | 8 mo |
| 4 (8 mo) | 33/M | Unknown | 1000 | 9 | 10 | 1.3 | <1 mo |

*parentheses show duration of follow-up from kidney transplant

FIGURE 2

COMBINED ORGAN AND HEMATOPOIETIC CELLS FOR TRANSPLANTATION TOLERANCE OF HLA MISMATCHED GRAFTS

BACKGROUND OF THE INVENTION

Advances in surgical technique and improved drugs to prevent infection and rejection have allowed transplantation of solid organs to become an effective treatment for many diseases. Transplanted organs include heart, intestine, liver, lung, pancreas and kidney. Kidney transplantation, or renal transplantation, is the organ transplant of a kidney into a patient with end-stage renal disease. Kidney transplantation can be classified as deceased or living-donor transplantation, and may further be classified according to the degree of relationship between donor and recipient, as related or non-related, and according to the number of HLA mismatches.

The indication for kidney transplantation is end-stage renal disease (ESRD), regardless of the primary cause, defined as a glomerular filtration rate below a pre-determined level. Common diseases leading to ESRD include malignant hypertension, infections, diabetes mellitus, and focal segmental glomerulosclerosis; genetic causes include polycystic kidney disease, a number of inborn errors of metabolism, and autoimmune conditions such as lupus. Diabetes is a common cause of kidney transplantation, accounting for approximately 25% of those in the US. The majority of renal transplant recipients are on dialysis at the time of transplantation.

The major barrier to organ transplantation between genetically non-identical patients lies in the recipient's immune system, which can respond to the transplanted kidney as "non-self" and reject it. Thus, having medications to suppress the immune system is essential, however, suppressing an individual's immune system places that individual at greater risk of infection and cancer, in addition to the side effects of the medications. Recipients usually receive a mixture of three maintenance immunosuppressive drugs, including a calcineurin inhibitor such as cyclosporine A, tacrolimus or sirolimus; prednisone; and an inhibitor of nucleic acid synthesis such as mycophenolate mofetil. The latter drugs have side effects that include hypertension, nephrotoxicity, infection, and heart disease that contribute to long term patient disability and graft loss. In spite of modern immunosuppressive drugs, in some centers acute rejection can occur in 10-25% of people after transplant.

Generally transplant recipients will take immunosuppressive anti-rejection drugs for as long as the transplanted kidney functions. Even for a mixture of widely used immunosuppressives the cost can be high.

It is therefore of great clinical interest to develop therapeutic regimens that achieve tolerance and complete withdrawal of immunosuppressive drugs in adult transplant patients. This approach has been explored in humans for HLA-matched transplantation, where the organ recipient becomes tolerant through co-transplantation of immune system cells (allogeneic hematopoietic cell transplantation, or HCT), which establish a state of chimerism. A danger exists, however, in the ability of the donor immune cells to generate a graft versus host disease. The development of persistent mixed chimerism and tolerance after bone marrow transplantation combined with organ transplantation in adult rodents and large laboratory animals has been achieved without graft versus host disease using non-myeloablative conditioning regimens.

Preclinical studies have shown that conditioning with total lymphoid irradiation (TLI) and anti-thymocyte globulin (ATG) is advantageous for inducing tolerance after combined organ and bone marrow transplantation because the conditioning regimen prevents GVHD as compared to total body irradiation (TBI). For a review, see Strober et al. (2011) Seminars in Immunology 23:273-281.

SUMMARY OF THE INVENTION

Methods and compositions are provided for combined transplantation of a solid organ and hematopoietic cells to an HLA mismatched recipient, where tolerance to the graft is established through development of a stable mixed chimera. Transplantation of kidneys is of particular interest. An individual with stable mixed chimerism, usually for a period of at least six months, is able to withdraw from the use of immunosuppressive drugs after a period of time sufficient to establish tolerance.

As used herein, the term "HLA mismatched" refers to typing of HLA-A, B and DR, such that the donor and recipient differ by at least one A, B, or DR antigen. In some such embodiments, an HLA-mismatched recipient is a haplotype matched recipient, where the donor and recipient are matched on one allele for HLA-A, HLA-B and HLA-DR, but are mismatched on the other allele, which combinations are frequently found where donor and recipient are related, e.g. sibling, parent and child, etc.

In the methods of the invention, following transplantation of a HLA mismatched solid organ, the recipient is treated with intravenous injections of ATG (anti-thymoglobulin), a total of 1000-1,200 cGy of total lymphoid irradiation, an infusion of donor hematopoietic cells, and a period of immunosuppression. The infusion of donor cells is engineered to contain at least $10 \times 10^6$ purified (to greater than 70% purity) $CD34^+$ cells/kilogram recipient weight; and sufficient numbers of $CD3^+$ cells cells/kilogram recipient weight to achieve mixed but not complete chimerism for at least 6 months. The dose of CD3+ cells to achieve mixed chimerism is in the range of $1.0-5.0 \times 10^7$ cell/kilogram. The immunosuppression is maintained for a period of time sufficient for the recipient to establish mixed chimerism of the hematopoietic system, usually for at least 6 months duration. Following establishment of mixed chimerism the recipient is tapered off immunosuppression between 9 to 15 months after transplantation and immunosuppressive drugs are discontinued.

In some embodiments, a method is provided for organ transplantation, comprising the steps of implanting a HLA-mismatched solid human organ in a recipient human body; treating the recipient with anti-thymoglobulin and total lymphoid irradiation; and infusing the recipient with an engineered donor hematopoietic cell product comprising at least $10^7$ purified $CD34^+$ cells/kilogram recipient weight; and from about $10-50 \times 10^6$ $CD3^+$ cells cells/kilogram recipient weight. In some embodiments, the recipient is monitored for mixed chimerism of the hematopoietic system during a maintenance period on an immunosuppressive regimen. In some embodiments, individuals demonstrated to have stable mixed chimerism of the hematopoietic system are withdrawn from the immunosuppressive regimen.

In some embodiments, a kit is provided for practice of the methods of the invention. A kit may include an engineered hematopoietic cell product comprising at least $10^7$ purified $CD34^+$ cells/kilogram recipient weight; and from about $10-50 \times 10^6$ $CD3^+$ cells cells/kilogram recipient weight; and instructions for use. Kits may further comprise reagents for assessment of mixed chimerism in a recipient.

BRIEF DESCRIPTION OF THE DRAWINGS

FIG. 2 is a table of results from haplotype matched organ transplants.

DETAILED DESCRIPTION OF THE EMBODIMENTS

Definitions

Figure 1:
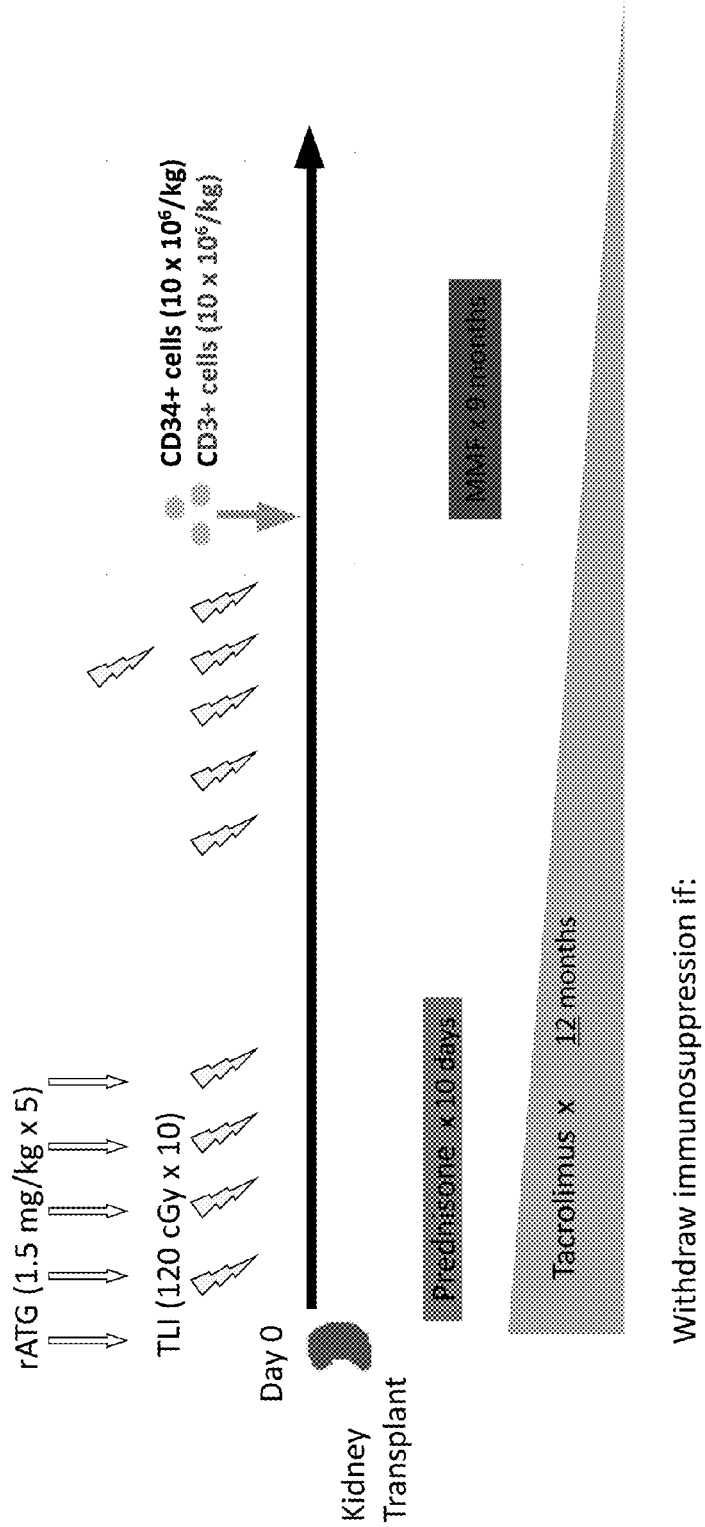
FIG. 1 illustrates a protocol for kidney and hematopoietic cell transplantation for a haplotype matched donor and recipient.
Figure 3:
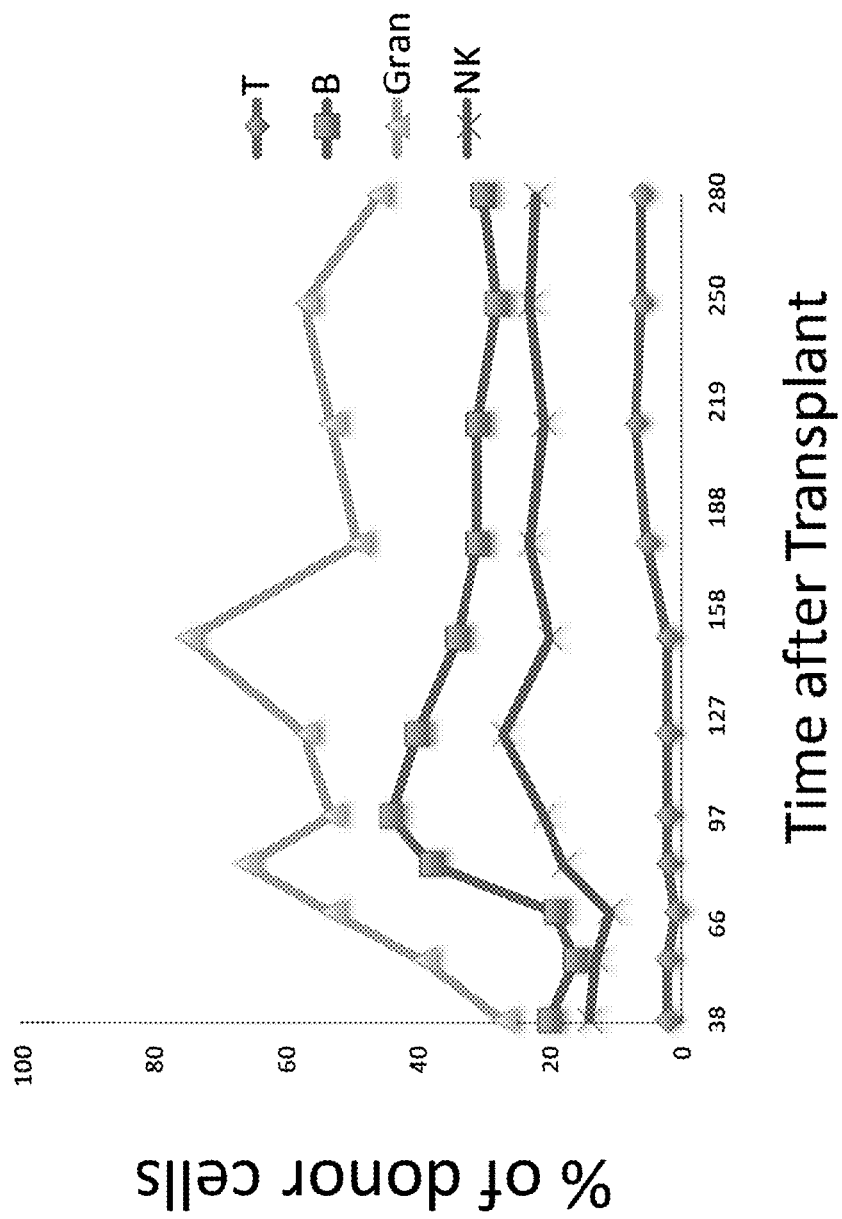
FIG. 3 provides a graph assessment of chimerism following haplotype matched combined organ transplant in patient #2 from FIG. 2.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention is established by the appended claims. In this specification and the appended claims, the singular forms "a," "an" and "the" include plural reference unless the context clearly dictates otherwise.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

As used herein, a recipient is an individual to whom an organ, tissue or cells from another individual (donor), commonly of the same species, has been transferred. For the purposes of the present invention, a recipient and a donor are HLA mismatched.

Major histocompatibility complex antigens (also called human leukocyte antigens, HLA) are protein molecules expressed on the surface of cells that confer a unique antigenic identity to these cells. MHC/HLA antigens are target molecules that are recognized by T-cells and natural killer (NK) cells as being derived from the same source of hematopoietic reconstituting stem cells as the immune effector cells ("self") or as being derived from another source of hematopoietic reconstituting cells ("non-self"). Two main classes of HLA antigens are recognized: HLA class I and HLA class II. HLA class I antigens (A, B, and C in humans) render each cell recognizable as "self," whereas HLA class II antigens (DR, DP, and DQ in humans) are involved in reactions between lymphocytes and antigen presenting cells. Both have been implicated in the rejection of transplanted organs.

An important aspect of the HLA gene system is its polymorphism. Each gene, MHC class I (A, B and C) and MHC class II (DP, DQ and DR) exists in different alleles. HLA alleles are designated by numbers and subscripts. For example, two unrelated individuals may carry class I HLA-B, genes B5, and Bw41, respectively. Allelic gene products differ in one or more amino acids in the $\alpha$ and/or $\beta$ domain(s). Large panels of specific antibodies or nucleic acid reagents are used to type HLA haplotypes of individuals, using leukocytes that express class I and class II molecules. The genes most important for HLA typing are the six MHC Class I and Class II proteins, two alleles for each of HLA-A; HLA-B and HLA-DR.

The human leukocyte antigen (HLA) genes are clustered in a "super-locus" present on chromosome position 6p21, which encodes the six classical transplantation HLA genes and at least 132 protein coding genes that have important roles in the regulation of the immune system as well as some other fundamental molecular and cellular processes. The complete locus measures roughly 3.6 Mb, with at least 224 gene loci. One effect of this clustering is that "haplotypes", i.e. the set of alleles present on a single chromosome, which is inherited from one parent, tend to be inherited as a group. The set of alleles inherited from each parent forms a haplotype, in which some alleles tend to be associated together. Identifying a patient's haplotypes can help predict the probability of finding matching donors and assist in developing a search strategy, because some alleles and haplotypes are more common than others and they are distributed at different frequencies in different racial and ethnic groups.

As used herein, the term "HLA mismatched" refers to a donor recipient pair in which at least one HLA antigen, in particular with respect to HLA-A, HLA-B and HLA-DR, is mismatched between the donor and recipient. In some embodiments one haplotype is matched and the other is mismatched. This situation is frequently found with organs from living or deceased donors. HLA mismatched donor/recipient pairs have an increased risk of graft v. host disease relative to perfectly matched pairs (i.e. where all 6 alleles are matched).

HLA alleles are typically noted with a variety of levels of detail. Most designations begin with HLA- and the locus name, then * and some (even) number of digits specifying the allele. The first two digits specify a group of alleles. Older typing methodologies often could not completely distinguish alleles and so stopped at this level. The third through fourth digits specify a synonymous allele. Digits five through six denote any synonymous mutations within the coding frame of the gene. The seventh and eighth digits distinguish mutations outside the coding region. Letters such as L, N, Q, or S may follow an allele's designation to specify an expression level or other non-genomic data known about it. Thus, a completely described allele may be up to 9 digits long, not including the HLA-prefix and locus notation.

Any method known in the art may be optionally used to for typing the cells. For example, three main processes are currently used to perform HLA typing. The first is conventional serological cytotoxicity method, where samples of lymphocytes (taken from blood or spleen) are added to Terasaki plates. These plates hold individual wells that contain different specific antibodies (from either maternal sera or manufactured monoclonal antibodies). The best cells for class II typing are B lymphocytes, and class I typing can be performed with the remaining leucocytes. Magnetic beads are used to purify the required cells from blood or spleen. If the HLA antigen and specific antibody bind, and complement is added, the cells in that well is killed. The pattern of wells showing this cell death allows the deduction of which combination of HLA antigens were present on the original tissue cells.

Another method used for HLA typing is flow cytometry, particularly when looking for specific alleles. Leucocytes are added to detectable labeled monoclonal antibodies specific for the HLA types of interest. The sample is then analyzed by flow cytometry to determine which antibodies have bound to the cells.

DNA typing is increasingly being used for HLA typing. This process involves extracting the DNA from cells and amplifying the genes that encode for the HLA peptides using polymerase chain reaction techniques. The genes may be matched with known HLA nucleotide sequences found stored in several gene bank databases, including the IMGT/HLA database.

As used herein, the term "solid organ transplantation" is used in accordance with the conventional meaning of the term, where an organ from a donor, which donor may be living or deceased, in placed into the body of a recipient in the appropriate position and cardiovascular connections to be physiologically integrated into the recipient. Transplantation of a kidney is of particular interest for the methods of the invention, although the methods do not exclude transplantation of other organs, e.g. pancreas and including pancreatic islet cells; heart; lungs, intestine, liver, and the like as known in the art. The transplanted organ may be referenced as a "graft", and the physiological integration of the organ may be referred to as engraftment.

Hematopoietic stem cell transplantation (HCT) is the transplantation of multipotent hematopoietic stem cells, usually derived from bone marrow, peripheral blood, or umbilical cord blood. For the methods of the invention, the hematopoietic cells are engineered into a product for infusion having a specific pre-determined number of purified ($\geq$70% purity) $CD34^+$ progenitor cells and $CD3^+$ T cells. The hematopoietic cells are obtained from the solid organ donor, and thus are HLA-identical to the solid organ, and HLA mismatched to the organ recipient.

Where the donor is deceased, hematopoietic cells may be obtained from bone marrow, e.g. vertebrae, pelvic bone, etc. Where the donor is a living donor, hematopoietic cells may be mobilized, e.g. with G-CSF, and collected by apheresis or similar methods. Alternatively, cells may be obtained from bone marrow, e.g. pelvic bone, etc.

Hematopoietic cells can be frozen (cryopreserved) for prolonged periods without damaging too many cells. To cryopreserve HSC, a preservative, DMSO, must be added, and the cells must be cooled very slowly in a controlled-rate freezer to prevent osmotic cellular injury during ice crystal formation. HSC may be stored for years in a cryofreezer, which typically uses liquid nitrogen.

The recipient's immune system is conditioned with a non-myeloablative procedure prior to infusion of the hematopoietic cells. Non-myeloablative transplants use doses of antibody and radiation that are too low to eradicate all the bone marrow cells of a recipient, thus enabling the desired goal of stable mixed chimerism where both recipient and donor HSC coexist in the bone marrow space. The conditioning regimen includes treatment with ATG (anti-thymocyte globulin); total lymphoid irradiation, and corticosteroids, e.g. prednisone, usually for a period of from about 10 to 12 days, e.g. for about 11 days.

Immunosuppression, as used herein, refers to the treatment of a graft recipient with agents, primarily to diminish the immune responses of the host immune system against the graft, although the agents may also diminish GVHD of the donor hematopoietic cells. Exemplary immunosuppression regimens are described in more detail herein, but will generally be conventional for a period of about 6 to 12 months. The recipient is tested for mixed chimerism of the hematopoietic system, and if found to have maintained mixed chimerism after at least 6 months, will be tapered off immunosuppression.

Immunosuppressive treatment of the transplantation patient begins with the induction phase, perioperatively and immediately after transplantation. Maintenance therapy then continues until withdrawal for individuals showing stable mixed chimerism. Induction and maintenance strategies use different medicines at specific doses or at doses adjusted to achieve target therapeutic levels to give the transplantation patient the best hope for long-term graft survival.

Primary immunosuppressive agents include calcineurin inhibitors, which combine with binding proteins to inhibit calcineurin activity, and which include, for example, tacrolimus, cyclosporine A, etc. Levels of both cyclosporine and tacrolimus must be carefully monitored. Initially, levels can be kept in the range of 10-20 ng/mL, but, after 3 months, levels may be kept lower (5-10 ng/mL) to reduce the risk of nephrotoxicity.

Adjuvant agents are usually combined with a calcineurin inhibitor and include steroids, azathioprine, mycophenolate mofetil, and sirolimus. Protocols of interest include a calcineurin inhibitor with mycophenolate mofetil. The use of adjuvant agents allows clinicians to achieve adequate immunosuppression while decreasing the dose and toxicity of individual agents. Mycophenolate mofetil in kidney transplant recipients has assumed an important role in immunosuppression after several clinical trials have shown a markedly decreased prevalence of acute cellular rejection compared with azathioprine and a reduction in 1-year treatment failures.

Antibody-based therapy uses monoclonal (eg, muromonab-CD3) or polyclonal antibodies or anti-CD25 antibodies (eg, basiliximab, daclizumab) and is administered in the early posttransplant period (up to 8 wk). Antibody-based therapy allows for avoidance or dose reduction of calcineurin inhibitors, possibly reducing the risk of nephrotoxicity. The adverse effect profile of the polyclonal and monoclonal antibodies limits their use in some patients.

Graft-versus-host disease (GVHD) is an inflammatory disease that is peculiar to transplantation of hematopoietic cells. It is an attack of the donor bone marrow's immune cells against the recipient's tissues. This can occur even if the donor and recipient are HLA-identical because the immune system can still recognize other differences between their tissues, and is of particular concern for haplotype-matched transplants. Acute graft-versus-host disease typically occurs in the first 3 months after transplantation and may involve the skin, intestine, or the liver. High-dose corticosteroids such as prednisone are a standard treatment. Chronic graft-versus-host disease may also develop after haplotype matched transplant. It is the major source of late treatment-related complications, although it less often results in death. In addition to inflammation, chronic graft-versus-host disease may lead to the development of fibrosis, or scar tissue, similar to scleroderma; it may cause functional disability and require prolonged immunosuppressive therapy. Graft-versus-host disease is usually mediated by T cells, which react to foreign peptides presented on the MHC of the host. The risk of GVHD is markedly reduced in patients with mixed instead of complete chimerism and achieving mixed chimerism is desirable for this reason. In addition, immunodeficiency and infection is more frequently observed in complete versus mixed chimerism.

"Acute rejection" is the rejection by the immune system of a transplanted organ. Acute rejection is characterized by infiltration of the transplanted tissue by immune cells of the recipient, which carry out their effector function and destroy the transplanted tissue. The onset of acute rejection is rapid and generally occurs in humans within a few weeks after transplant surgery. Generally, acute rejection is inhibited or suppressed with immunosuppressive drugs. Steroids are the mainstay of therapy for acute rejection episodes. The typical dosage is 3-5 mg/kg/d for 3-5 days, which is then tapered to a maintenance dose. Antithymocyte globulin and muromonab-CD3 also find use.

"Chronic transplant rejection" generally occurs in humans within several months to years after engraftment, even in the presence of successful immunosuppression of acute rejection. Fibrosis is a common factor in chronic rejection of all types of organ transplants. Chronic rejection can typically be described by a range of specific disorders that are characteristic of the particular organ. For example, in lung transplants, such disorders include fibroproliferative destruction of the airway (bronchiolitis obliterans); in heart transplants or transplants of cardiac tissue, such as valve replacements, such disorders include fibrotic atherosclerosis; in kidney transplants, such disorders include, obstructive nephropathy, nephrosclerorsis, tubulointerstitial nephropathy; and in liver transplants, such disorders include disappearing bile duct syndrome. Chronic rejection can also be characterized by ischemic insult, denervation of the transplanted tissue, hyperlipidemia and hypertension associated with immunosuppressive drugs. Unless inadequate immunosuppression is the cause of rejection, changes in immunosuppressive therapy are generally not effective in reversing chronic rejection. Control of blood pressure, treatment of hyperlipidemia, and management of diabetes are the current mainstays of treatment for graft preservation.

The term "transplant rejection" encompasses both acute and chronic transplant rejection.

Hematopoietic cell transplant loss may be defined as either the absence of hematopoietic reconstitution of donor origin on day +45 after the allograft (primary graft rejection) or as confirmed loss of donor cells after transient engraftment of donor-origin hematopoiesis. Kidney graft failure can be defined as either the creatinine clearance declining to less than 10 ml/min or the return of the patient to dialysis, or the return of the patient to the transplant list for retransplantation.

Chimerism, as used herein, generally refers to chimerism of the hematopoietic system, unless otherwise noted. A determination of whether an individual is a full chimera, mixed chimera, or non-chimeric made be made by an analysis of a hematopoietic cell sample from the graft recipient, e.g. peripheral blood, bone marrow, etc. as known in the art. Analysis may be done by any convenient method of typing. In some embodiments the degree of chimerism amongst all mononuclear cells, T cells, B cells, $CD56^+$ NK cells, and $CD15^+$ neutrophils is regularly monitored, using PCR with probes for microsatellite analysis. For example, commercial kits that distinguish polymorphisms in short terminal repeat lengths of donor and host origin are available. Automated readers provide the percentage of donor type cells based on standard curves from artificial donor and host cell mixtures.

Individuals who exhibited more than a 95% donor cells in a given blood cell lineage by such analysis at any time post-transplantation are referred to as having full donor chimerism in this transplant patient group. Mixed chimerism is defined as greater than 1% donor but less than 95% donor DNA in such analysis. Individuals who exhibit mixed chimerism may be further classified according to the evolution of chimerism, where improving mixed chimerism is defined as a continuous increase in the proportion of donor cells over at least a 6-month period. Stable mixed chimerism is defined as fluctuations in the percentage of recipient cells over time, without complete loss of donor cells. Candidates for withdrawal of immunosuppression have mixed chimerism until at least 6 months post-transplantation.

"Diagnosis" as used herein generally includes determination of a subject's susceptibility to a disease or disorder, determination as to whether a subject is presently affected by a disease or disorder, prognosis of a subject affected by a disease or disorder (e.g., identification of pre-metastatic or metastatic cancerous states, stages of cancer, or responsiveness of cancer to therapy), and use of therametrics (e.g., monitoring a subject's condition to provide information as to the effect or efficacy of therapy).

The term "biological sample" encompasses a variety of sample types obtained from an organism and can be used in a diagnostic or monitoring assay. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

The terms "individual," "subject," "host," and "patient," used interchangeably herein and refer to any mammalian subject for whom diagnosis, treatment, or therapy is desired, particularly humans.

The term "graft management" refers to therapeutic methods that induce and/or promote repair engraftment of a solid organ, but not limited to, kidney transplantation.

The term "pharmaceutically acceptable" as used herein refers to a compound or combination of compounds that will not impair the physiology of the recipient human or animal to the extent that the viability of the recipient is compromised. Preferably, the administered compound or combination of compounds will elicit, at most, a temporary detrimental effect on the health of the recipient human or animal.

The term "carrier" as used herein refers to any pharmaceutically acceptable solvent of agents that will allow a therapeutic composition to be administered directly to a wound of the skin. The carrier will allow a composition to be topically applied to an exposed surface of an organ for transplantation and the site of the recipient where the organ is to be placed. A "carrier" as used herein, therefore, refers to such solvent as, but not limited to, water, saline, oil-water emulsions, or any other solvent or combination of solvents and compounds known to one of skill in the art that is pharmaceutically and physiologically acceptable to the recipient human or animal.

The term "assessing" and "evaluating" are used interchangeably to refer to any form of measurement, and includes determining if an element is present or not. The terms "determining," "measuring," "assessing," and "assaying" are used interchangeably and include both quantitative and qualitative determinations. Assessing may be relative or absolute. "Assessing the presence of" includes determining the amount of something present, as well as determining whether it is present or absent.

Methods of the Invention

The methods of the invention may comprise the steps of: HLA typing a donor and recipient to determine an HLA mismatched pair such as at least 1 of 6 HLA antigens (HLA-A, B, DR) are mismatched; obtaining the solid organ and hematopoietic cells from the donor; isolating hematopoietic cells of the appropriate type and dose; transplanting the solid organ; performing a conditioning regimen on the recipient following transplantation of the solid organ and prior to infusion of the engineered hematopoietic cells; maintaining the recipient on an immunosuppressive regimen for at least about 6 months; monitoring the recipient for mixed chimerism of the hematopoietic system; and withdrawing immunosuppression if the recipient shows stable mixed chimerism. These steps will be discussed in detail below.

Individuals selected for the methods of the invention meet the criteria of (i) requiring a solid organ graft; and (ii) having an HLA mismatched donor from which the solid organ and hematopoietic cells can be obtained. By performing a combined transplant of solid organ and an engineered hematopoietic cell infusion appropriate for the individual, in combination with non-myeloablative conditioning, the patient has a high probability of developing persistent mixed chimerism for at least 6 months, which allows for withdrawal of immunosuppression over time.

The solid organ is harvested and transplanted in accordance with conventional practice. Hematopoietic cells are obtained from the donor by various methods known in the art, including apheresis of mobilized peripheral blood from living donors; harvesting hematopoietic cells from bone marrow of deceased donors, and the like. The solid organ is transplanted 10-12 days prior to the infusion of the engineered hematopoietic cells, and thus for most purposes the hematopoietic cells are cryopreserved after engineering.

A single intravenous infusion of cryopreserved HLA mismatched donor hematopoietic cells is "engineered" for administration following the course to TLI or multiple doses of radiation targeted to the lymphoid tissue. The donor hematopoietic cells are selected for expression of CD34 by selectively binding a suitable CD34 affinity reagent, e.g. antibody, to the population of hematopoietic cells. The CD34+ cells are collected by any convenient method, e.g. Miltenyi columns, flow cytometry, magnetic selection, etc. as is known in the art. The target dose of CD34$^+$ cells to be injected is $\geq 10 \times 10^6$ cells/kg. The CD3+ cells may be selected separately, but for convenience the flow-through from the CD34 selection process can be used, where the dose of flow through cells are calculated based on the content of CD3$^+$ cells determined by immunofluorescent staining to provide a defined dose of about $1-5 \times 10^7$/kg CD3$^+$ T cells, usually about $1-2 \times 10^7$/kg CD3+ cells, more usually about $1 \times 10^7$/kg CD3$^+$ T cells. Typically the CD34+ cells and the CD3+ cells are separately cryopreserved, and the target doses prepared for infusion upon thawing. The defined doses of CD34+ cells are selected to achieve mixed chimerism for at least 6 months.

Following transplantation of the solid organ, the recipient is treated with non-myeloablative conditioning. Patients receive a total of 5 intravenous doses of thymoglobulin (ATG) over a 5 day period; each dose is 1.5 mg/kg. Thymoglobulin is administered on the day of transplantation (intra-operatively before the transplanted organ is perfused with host blood) and on the subsequent 4 days post-transplant. Alternatively any T cell depleting agent can be used including anti-T cell monoclonal antibodies or T cell depleting drugs such as fludarabine. Patients also receive ten treatments of fractionated irradiation (100-120 cGy each) targeted to the lymph nodes, spleen and thymus gland on days 1 through 4, and days 7 through 11, after transplantation such that the total dose of TLI is 1000-1,200 cGy. Two doses are given on day 10 or 11 to achieve a total of 10 doses. During the administration of TLI, patients can be monitored for the development of neutropenia (granulocytes <2,000/mL), thrombocytopenia (platelets <60,000/mL) and infection. TLI is withheld for any of these problems, and G-CSF (10 µg/kg/day) is given for neutropenia. TLI is reinstated once neutropenia and/or thrombocytopenia resolves. At the completion of TLI, all patients are given G-CSF (10 µg/kg/day) if the white blood cell count is below 1,000 cells/mm$^3$. TLI is completed by day 11 if no doses are withheld. The engineered hematopoietic cell product is infused into the patient at the completion of TLI. Any form of radiation given in multiple doses targeted to the lymphoid tissues can be an alternative to TLI.

The hematopoietic cells are administered in any physiologically acceptable excipient, where the cells may find an appropriate site for regeneration and differentiation. The cells may be introduced by injection, catheter, or the like. The cells may be frozen at liquid nitrogen temperatures and stored for long periods of time, being capable of use on thawing. If frozen, the cells will usually be stored in a 10% DMSO, 50% FCS, 40% RPMI 1640 medium. Once thawed, the cells may be expanded by use of growth factors and/or feeder cells associated with progenitor cell proliferation and differentiation.

The cells of this invention can be supplied in the form of a pharmaceutical composition, comprising an isotonic excipient prepared under sufficiently sterile conditions for human administration. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000. Choice of the cellular excipient and any accompanying elements of the composition is adapted in accordance with the route and device used for administration. The composition may also comprise or be accompanied with one or more other ingredients that facilitate the engraftment or functional mobilization of the cells. Suitable ingredients include matrix proteins that support or promote adhesion of the cells, or complementary cell types, especially endothelial cells.

Corticosteroid therapy may be given as premedication on the days of ATG infusions to reduce ATG side effects, at a dose of from 60-120 mg, e.g. as Solumedrol (I.V.). After the last dose of ATG, a tapering course of prednisone starting at 30 mg/d and reducing by 5 mg/d may be given until day 30 to reduce the risk of rejection.

The patient is treated with a suitable immunosuppressive regimen following the donor cell infusion. Suitable agents include a calcineurin inhibitor, for example, tacrolimus, cyclosporine A, etc. and adjuvant agent, for example steroids, azathioprine, mycophenolate mofetil, sirolimus, antibodies, etc. Protocols of interest include a calcineurin inhibitor with purine metabolism inhibitor such as mycophenolate mofetil (MMF), e.g. cyclosporine and MMF are particularly suitable for kidney transplantation. The MMF adjuvant may be stopped after about 6 to 9 months. The calcineurin inhibitor is slowly tapered, providing the recipient meets clinical criteria for lack of rejection and GVHD, such that after about 12 months the dase has been tapered to zero. An initial dose will be conventional, e.g. around about 5 mg/kg twice a day, adjusted to achieve a whole blood trough level of 350-450 ng/ml. Alternative immunosuppressive drugs or biological reagents can be used instead of calcineurin and purine metabolism inhibitors.

In order to determine if tapering of the immunosuppressive regimen is appropriate for the recipient, the recipient will be tested for mixed chimerism, usually at regular intervals, for example monthly, semi-monthly, weekly, bimonthly, etc. Methods of testing for chimerism are readily available, using any method that distinguishes whether a cell is of donor or recipient origin. Conveniently, PCR with probes for microsatellite analysis may be used. For example, commercial kits that distinguish polymorphisms in short terminal repeat lengths of donor and host origin are available. Alternatively, MHC typing can be used to test the type of blood cells, for example in combination with flow cytometry analysis of HLA-stained blood cells. Other such methods are readily available to one of skill in the art. Mixed chimerism is defined as greater than 1% recipient DNA in such analysis. Typically guidelines for complete drug withdrawal include mixed chimerism persisting for at least 6 months, lack of rejection episodes, and lack of GVHD.

The invention now being fully described, it is apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It is appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

For further elaboration of general techniques useful in the practice of this invention, the practitioner can refer to standard textbooks and reviews in cell biology, tissue culture, and embryology. With respect to tissue culture and embryonic stem cells, the reader may wish to refer to Teratocarcinomas and embryonic stem cells: A practical approach (E. J. Robertson, ed., IRL Press Ltd. 1987); Guide to Techniques in Mouse Development (P. M. Wasserman et al. eds., Academic Press 1993); Embryonic Stem Cell Differentiation in Vitro (M. V. Wiles, Meth. Enzymol. 225:900, 1993); Properties and uses of Embryonic Stem Cells: Prospects for Application to Human Biology and Gene Therapy (P. D. Rathjen et al., Reprod. Fertil. Dev. 10:31, 1998).

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and ClonTech.

Example 1

TLI and ATG Conditioning for Combined Kidney and Blood Stem Cell Transplantation Immune tolerance to HLA haplotype matched living related donor kidney allografts is developed in order to remove the requirement for the lifelong use of immunosuppressive drugs and to improve the long term graft survival. Currently, these haplotype matched recipients account for about half of living related donor kidney transplants performed at most medical centers in the United States. During the past 10 years an increasing proportion of grafts in most centers were from living related donors as an alternative to cadaver grafts. Although the living related donor transplants have improved survival as compared to cadaver transplants, about 40 to 50% of the living donor grafts are still lost within about 10 years. In addition, the recipients usually receive a mixture of 3 maintenance immunosuppressive drugs including a calcineurin inhibitor, prednisone, and mycophenolate mofetil. The latter drugs have side effects that include hypertension, nephrotoxicity, and heart disease that contribute to long term patient disability and graft loss.

Our preclinical studies showed that conditioning with TLI and ATG is advantageous for inducing tolerance after combined organ and bone marrow transplantation because the conditioning regimen prevents GVHD as compared to TBI. Approximately 1,000 fold more donor T cells are needed to induce lethal GVHD using TLI/ATG as compared to TBI conditioning. The basis of protection against GVHD is the change in the balance of residual host T cells that favors the host natural killer (NK) T cell subset. The latter cells become the predominant T cell subset in TLI/ATG conditioned mice and produce large amounts of IL-4 that polarize conventional donor T cells toward a Th2 bias, thereby attenuating GVHD. Several laboratories have shown that NK T cells that survive in vivo irradiation are themselves polarized toward a Th2 bias.

Based on the protective effect of TLI/ATG against GVHD in the preclinical studies, this conditioning regimen has been successfully tested as a non-myeloablative regimen for HLA matched cell transplantation for patients. Modifications were made in the conditioning regimen and make-up of the hematopoetic cell graft for the adaptation. The hematopoietic cell graft was "engineered" to contain a defined number of purified CD34$^+$ hematopoietic progenitor cells selected by immunomagnetic bead columns and a defined number of donor T cells. Other aspects of the conditioning regimen remained the same, including the TLI and ATG schedule. A post-transplant immunosuppressive regimen of 1 month of MMF and 6 months of cyclosporine was adapted from standard protocols for patients receiving hematopoietic cell transplants to treat leukemia and lymphoma. Of note, the conditioning regimen was performed with the start of transplant surgery on day 0, and infusion of donor hematopoietic cells was administered on day 11. This allowed for the further adaptation of the protocol to cadaver transplants in the future, and was the schedule used in the numerous preclinical studies of combined transplantation using TLI/ATG.

Twenty patients were given combined HLA matched grafts, followed up from between 5 to 86 months. Nineteen of these became chimeras without the development of GVHD. Seventeen developed persistent chimerism (>6 months), and of these 14 were withdrawn from immunosuppressive drugs, 2 of the 17 patients are undergoing drug tapering, and 4 of 20 failed drug withdrawal (either due to failure to maintain chimerism for >6 months, or due to rejection episodes). All 20 patients currently had excellent graft function at the last observation point, and were discharged about 5 hospital days after transplant surgery. The patients needed 3-16 CD34+ cell/kg and $1\times10^6$ CD3+ cell/Kg.

In order to apply the tolerance protocol described above to HLA mismatched patients, adjustments in the doses of CD34+ and CD3+ donor cells were made based on preliminary studies of 17 HLA halotype mismatched patients who were given the TLI and ATG conditioning regimen and a donor cell transplant to treat leukemia or lymphoma. The dose of CD34+ cells was gradually escalated to $\geq 10\times10^6$ cell/Kg and the CD3+ dose was gradually escalated to $10\times10^6$ cells/kg. The majority of patients given the latter cell dose achieved mixed chimerism whereas none of the patients given cell doses lower than these levels achieved mixed chimerism. Accordingly, a dose escalation clinical study was performed on 4 HLA haplotype matched patients given combined kidney and hematopoietic cell transplants with the goal of achieving target doses of $\geq 10\times10^6$/Kg CD34+ cells and $\geq 10\times10^6$/Kg CD3+ cells. The purpose of the study was to determine whether the achievement of these target doses would result in the development of mixed chimerism for >6 months and the ability to withdraw immunosuppressive drugs thereafter. Some details of the clinical protocol are given below.

The gene array testing indicates that there is a change in the pre to post-transplant gene expression profiles in patients who met drug withdrawal criteria such that their profiles became considerably better matched to those of the rare "operationally" tolerant patients who stopped conventional immunosuppressive drugs and did not develop graft rejection at their first monitoring time point. This was not the case with the patients who failed to meet withdrawal criteria. The differences in gene expression pattern between the 2 groups decreased at later time points. It should be noted that the "operationally" tolerant patients were all HLA mismatched. This indicates that the tolerant gene expression profiles can be used to predict the tolerant state in both matched and mismatched patients.

Clinical Protocol

This was a single-center, open-label study in adult renal transplant patients. Patients received TLI, RATG and an infusion of G-CSF "mobilized blood" mononuclear cells that had been enriched for CD34$^+$ cells and contained a defined number of CD34$^+$ and CD3$^+$ donor cells. Immunosuppressive drugs consisted of 9 months of mycophenolate mofetil (MMF; 15 mg/Kg twice per day starting on day 10), and a tapering course of daily tacrolimus starting on day 0 that is discontinued at a target of 12 months. The immunosuppressive drug combination of a calcineurin inhibitor and a purine metabolism inhibitor was similar to that used previously. At serial time points (1) graft function was monitored, (2) chimerism was measured in recipient white blood cell subsets and (3) protocol biopsies of the graft is obtained. If chimerism failed to develop or is lost during the first six months, or if a rejection episode or GVHD occurred or if there was histological evidence of rejection in graft biopsies then tacrolimus and/or MMF was not withdrawn, and the patient would be followed thereafter as a treatment failure. Recipients in the study were given a target dose of $\geq 10\times10^6$ CD34$^+$ cells/Kg and an escalating dose of T cells to achieve the target dose of $1\times10^7$/Kg T cells from the "mobilized" peripheral blood mononuclear cells harvested from the donor. Of the 4 patients enrolled in the protocol, 2 did not receive the target cell doses and 2 did (Table 1).

Study Therapies.

During the course of this study, patients receive 5 intravenous injections of rabbit ATG (Thymoglobulin), a total of 1,200 cGy of total lymphoid irradiation, a single infusion of donor cells, transient immunosuppression (MMF and Tacrolimus), and prophylactic anti-viral, anti-fungal and antibacterial agents.

Patients receive a total of 5 intravenous doses of Thymoglobulin over a 5 day period; each dose is 1.5 mg/kg. Thymoglobulin is administered on the day of transplantation (intra-operatively before the transplanted organ is perfused with host blood) and on the subsequent 4 days post-transplant.

Patients receive ten treatments of fractionated irradiation (120 cGy each) targeted to the lymph nodes, spleen and thymus gland on days 1 through 4, and days 7 through 11, after transplantation such that the total dose of TLI is 1,200 cGy. Two doses are given on day 10 or 11 to achieve a total of 10 doses. TLI is given to the inverted Y and mantle fields. During the administration of TLI, patients are monitored for the development of neutropenia (granulocytes <2,000/mL), thrombocytopenia (platelets <60,000/mL) and infection. TLI is withheld for any of these problems, and G-CSF (10 μg/kg/day) is given for neutropenia. TLI is reinstated once neutropenia and/or thrombocytopenia resolves. At the completion of TLI, all patients are given G-CSF (10 μg/kg/day) if the white blood cell count is below 1,000 cells/mm$^3$. TLI is completed by day 11 if no doses are withheld.

A single intravenous infusion of cryopreserved HLA-haplotype matched living related donor, G-CSF mobilized blood mononuclear cells (recovered from donor peripheral blood using apheresis), that has been "engineered" is administered to patients on the day of completion of TLI. Harvesting of donor cells is performed in the following fashion: Approximately 6 weeks before renal transplantation, the donor is given G-CSF daily (16 mg/kg/day) for five days, and mononuclear cells are harvested by an apheresis of up to 20 liters according to procedures previously approved by the Stanford Committee on Medical Human Subjects for HLA-haplotype matched peripheral blood stem cell (PBSC) transplantation. In addition, a second session of up to 12 liters may be carried out for optimal cell recovery. Cells are selected for CD34$^+$ cells on Isolex columns, Column flow through is collected also. Both CD34$^+$ cells and flow through cells are cryopreserved and thawed according to standard procedures at the Stanford Blood and Marrow Transplantation laboratory. The target dose of CD34$^+$ cells to be injected is 10×10$^6$ cells/kg. A defined target dose of (1×10$^7$/kg CD3$^+$) T cells is administered by injecting column flow through cells along with enriched CD34$^+$ cells intravenously. The dose of flow through cells are calculated based on the content of CD3$^+$ cells determined by immunofluorescent staining. This dose was used in the 17 haplotype matched patients with leukemia and lymphoma. The majority of these patients developed persistent mixed chimerism, and none developed acute GVHD. The dose of T cells is increased if the first 3 recipients of combined transplants fail to achieve persistent chimerism, and is decreased if the first 3 recipients develop complete chimerism or if any patient develops GVHD.

Corticosteroid therapy was limited to 60-120 mg Solumedrol (I.V.) as premedication on the days of ATG infusions to reduce ATG side effects. After the last dose of ATG, a tapering course of prednisone starting at 30 mg/d and reducing by 5 mg/d is given until day 10.

MMF therapy commenced on the day of the donor cell infusion (day 10) at 15 mg/Kg twice per day. MMF therapy was maintained for 6 months, and then tapered and stopped at 9 months.

Tacrolimus was started on day 0, adjusted to achieve a standing whole blood trough level. As long as the criteria for immunosuppressive drug tapering are met, Tacrolimus was tapered beginning at month 9, and stopped by month 12.

Criteria for continued tapering of immunosuppressive drugs (Tacrolimus) through month 12 and MMF through month 9 were as follows: 1) Sustained chimerism for at least 6 months; 2) No clinical rejection episodes; 3) Protocol biopsies show no evidence of acute or chronic rejection; 4) No GVHD. Patients who do not meet these criteria are considered treatment failures, and further tapering of drugs is not performed.

If acute or chronic GVHD is observed that would ordinarily be treated with immunosuppressive drugs, then the patient is considered a treatment failure. Immunosuppressive drugs are administered according to standard practice.

Rejection episodes are treated with standard anti-rejection therapy which includes the use of intravenous methyl prednisolone and the patient is considered a treatment failure. If no response to two courses of steroids is found, then a course of anti-lymphocyte antibody is given. Tacrolimus is given at conventional doses during rejection episodes. Once a rejection episode occurs, patients will return to conventional doses of maintenance immunosuppressive drugs and no further tapering is attempted as per the protocol above. Currently 95% of acute rejection episodes are reversed.

Since the initial course of TLI and ATG is expected to induce a marked depletion of T cells, there is an increased risk of new or recrudescent viral infection, including cytomegalovirus (CMV), Epstein-Barr virus, Herpes zoster and Herpes simplex viruses as compared to conventional immunosuppressive protocols. Anti-viral prophylaxis for CMV is given as follows: Valganciclovir (900 mg/d:P.O.) was given for the first 14 days adjusted for renal function or during the first 14 days, ganciclovir (DHPG), 5 mg/kg, is given IV adjusted for renal function. After the 14-day course all protocol transplant recipients were placed on the valganciclovir (900 mg/d) adjusted for renal function. This was continued for a minimum of 90 days and if the absolute lymphocyte count is under 400, is continued until the time of steroid discontinuation.

Bactrim (1 single strength tablet per day) was given orally for one year for prophylaxis of *Pneumocystis carinii* pneumonia (PCP) and Mycostatin mouthwashes daily for three weeks for *candida* prophylaxis. Standard peri-operative antibiotics will include Ancef (1 mg, i.v., 3 doses at 8-hour intervals) and Gentamicin (1.7 mg/kg, i.v., one dose at the time of transplant). Antibacterial agents are subject to appropriate substitution according to patient allergies.

A surveillance biopsy is performed just before all immunosuppressive drugs are stopped posttransplant. In addition, "for-cause" biopsies are obtained within 48 hours of an unexplained or unresolved 20% increase in serum creatinine.

Of the two patients who failed to receive the targeted cell doses, patient #1 failed to have mixed chimerism persist for more than 1 month. This patient received 3×10$^6$ CD3+ cells/Kg as part of the dose escalation study, but did receive the targeted number of CD34+ cells/Kg. This patient was not withdrawn from immunosuppressive drugs, and remains on Tacrolimus and MMF with good graft function.

Patients #2 and #3 received the targeted cell dose of CD3+ T cells (10×10$^6$ cells/Kg) and the targeted dose of CD34+ cells. Both patients developed persistent mixed chimerism for 10 months and 5 months respectively at present, and meet drug withdrawal criteria. The pattern of persistent mixed chimerism is shorter for patient #3 in FIG. 2.

Patient #4 received 10×10$^6$ CD3+ cells/Kg but did not meet the requisite number of CD34+ cells due to poor mobilization of the donor CD34+ cells despite two courses of G-CSF administered to the donor. This patient failed to develop chimerism, and remains on immunosuppressive drugs with good graft function.

What is claimed is:

1. A method for transplantation of a HLA mismatched solid human organ, said method comprising:
   implanting said HLA mismatched solid human organ in a recipient human body, wherein said HLA mismatched solid human organ is from a donor;
   treating said recipient with non-myeloablative conditioning;
   infusing said recipient with an engineered hematopoietic cell composition, said engineered hematopoietic cell composition comprising at least $1\times10^7$ CD34$^+$ cells/kilogram recipient weight and at least $1\times10^7$ CD3$^+$ T cells/kilogram recipient weight; and maintaining said recipient on an immunosuppressive regimen for a period of time sufficient to develop mixed chimerism for at least 6 months.

2. The method of claim 1, wherein said HLA mismatched solid human organ is selected from a group consisting of a kidney, a heart, an intestine, a liver, a lung, and a pancreas.

3. The method of claim 1, wherein said engineered hematopoietic cell composition comprises about $5\times10^7$ CD3$^+$ T cells/kilogram recipient weight.

4. The method of claim 1, wherein said non-myeloablative conditioning comprises lymphoid tissue irradiation in combination with T cell depleting antibodies or drugs.

5. The method of claim 1, wherein said immunosuppressive regimen comprises a calcineurin inhibitor or a purine metabolism inhibitor, or said calcineurin inhibitor and said purine metabolism inhibitor, and wherein said recipient is maintained on said immunosuppressive regimen for a period of at least six months.

6. The method of claim 1, further comprising the step of:
monitoring said recipient for a stable mixed chimerism, wherein said stable mixed chimerism is defined as one of the following: (i) having at least 1% and less than 95% circulating donor hematopoietic cells, (ii) having at least 1% and less than 95% circulating immune cells or, (iii) having at least 1% and less than 95% of combined circulating hematopoietic cells and immune cells.

7. The method of claim 1, wherein said immunosuppressive regimen is withdrawn from said recipient found to have said mixed chimerism for at least six months.

8. The method of claim 1, wherein said donor is living or deceased.

9. The method of claim 1, wherein said CD34$^+$ cells are isolated and purified from said donor.

10. The method of claim 1, wherein said CD34$^+$ cells are purified to a purity of greater than 70%.

11. The method of claim 1, wherein a ratio of said CD3$^+$ T cells to said CD34$^+$ cells is at least 1.

12. The method of claim 1, wherein said HLA-mismatched solid human organ comprises at least one of HLA-A, HLA-B and HLA-DR that are different between said donor and said recipient.

* * * * *